United States Patent

Fallick

[11] Patent Number: 6,159,481
[45] Date of Patent: Dec. 12, 2000

[54] SWEAT RESISTANT SUNBLOCK AND ANTIOXIDANT COMPOSITION

[76] Inventor: Harry Fallick, 677 N. DeKalb Pike, King of Prussia, Pa. 19406

[21] Appl. No.: 09/046,087

[22] Filed: Mar. 23, 1998

Related U.S. Application Data

[63] Continuation-in-part of application No. 08/764,481, Dec. 12, 1996, abandoned.
[51] Int. Cl.⁷ ................................. A61K 7/42; A61K 7/44
[52] U.S. Cl. ................................. 424/401; 424/59; 424/60
[58] Field of Search ................................. 424/401, 59, 60

[56] References Cited

U.S. PATENT DOCUMENTS

| | | | |
|---|---|---|---|
| 5,468,471 | 11/1995 | Zecchino et al. | 424/59 |
| 5,520,917 | 5/1996 | Mizuguchi et al. | 424/401 |
| 5,560,917 | 10/1996 | Cohen et al. | 424/401 |

*Primary Examiner*—Donna Wortman
*Assistant Examiner*—Mary K. Zeman
*Attorney, Agent, or Firm*—John Lezdey & Assoc

[57] ABSTRACT

A sweat resistant sunblock and antioxidant composition for protection against a broad spectrum of radiation. The composition contains micronized and ultramicronized titanium particles, micronized dermatologically acceptable metal oxides, micronized talc, sunblocking polymers, antioxidants and a selenium yeast complex.

4 Claims, No Drawings

SWEAT RESISTANT SUNBLOCK AND ANTIOXIDANT COMPOSITION

This application is a continuation in part of Ser. No. 08/764,481 filed Dec. 12, 1996 abandoned.

FIELD OF THE INVENTION

The technical field of this invention is compositions and methods for treating skin to reduce the risk of skin damage caused by sunlight or other sources of ultraviolet radiation without forming a visible mask and is sweat resistant. There is further provided a means for reducing oxidative damage to the skin and means for increasing the SPF of sunblocking formulations.

BACKGROUND OF THE INVENTION

Skin damage such as cancer is a prevalent disease in humans caused by overexposure to ultraviolet radiation from the sun and other sources. It is commonly known that people with dark skin, or skin that easily tans, are less likely to develop skin cancer due to sunlight exposure. This reduced risk of sunlight-induced cancer is apparently due to the protective nature of melanin against ultraviolet light, and the relatively higher concentrations of melanin in the skin of darker skinned peoples. Current methods for reducing the risk of skin cancer caused by sunlight usually involve the control or elimination of sunlight exposure. Examples include mechanical blocking of the sun's rays, or chemical screening of the sun's rays, such as by using the ultraviolet sunscreen ingredient para-amino benzoic acid (PABA). Although such approaches appear to reduce the risk of sunlight and other ultraviolet radiation induced skin cancer, there remains a need for additional methods of treatment, particularly methods which are effective for treatment after exposure to the ultraviolet light.

PABA may affect some individuals adversely, particularly those with photosensitivity who are taking certain drugs. For these people use of opaque creams, pastes and lotions is advisable.

Ultraviolet radiation and the atmosphere also causes oxidative damage to the skin as to cause dryness, loss of elasticity and wrinkles. The use of sunblocking pigments is well known, however, these pigments such as zinc and iron oxide when used alone have a drying effect.

These pigments have often been used in compositions in large particle size and in a form which is a mask and used primarily by skiers and on beaches. However, such compositions have only found use on the face and particularly on the nose.

Other pigment formulations do not provide a broad spectrum of protection when used in a form and an amount where they are not perceivable on the user.

It is therefore desirable to provide a sunblocking composition which can achieve maximum full spectrum protection throughout the entire UVB–UVA range plus visible and infrared which does not cause damage to the skin but provides an antioxidant effect.

It is further desirable to provide a sunblocking formulation which can be used by people on the beach and those requiring environmental protection following a surgical trauma.

SUMMARY OF THE INVENTION

According to the present invention, there is provided a sweat resistant composition for protection against ultraviolet and infrared radiation which also reduces acute oxidation damage to the skin. The composition comprises:

- A. about 8.5 to 17.5% by weight of a plurality of micronized and ultramicronized titanium dioxide particles having a variety of particle sizes not more than 10 microns;
- B. about 0.5 to 2.5% by weight of a plurality of dermatologically acceptable iron and zinc oxides having a particle size not more than 10 microns;
- C. about 0.5 to 1.5% by weight of talcum having a particle size less than 10 microns;
- D. about 4.5 to 10% by weight of antioxidants;
- E. about 0.5 to 5% by weight of a water soluble polymer which blocks ultraviolet radiation;
- F. a selenium yeast complex; and
- G. at least one aqueous topical vehicle selected from the group consisting of ointments, suspensions, creams, lotions and emulsions.

The compositions provide an average SPF of at least about 70.

Advantageously, the composition contains non-para aminobenzoic acid UV absorbers and a selenium protein complex.

It is therefore an object of the invention to provide a sweat resistant sunblocking formulation which protects over a large range of radiation wavelengths.

It is another object of the invention to provide a U.V. blocking formulation for use by parties suffering a skin trauma.

It is yet another object of the invention to provide a sunblocking formulation which reduces oxidative damage to the skin.

DESCRIPTION OF THE PREFERRED EMBODIMENTS

The sweat resistant sunblocking and antioxidative compositions of the invention comprise:

- A. about 8.5 to 17.5% by weight of micronized and ultramicronized titanium dioxide particles having a variety of the different sizes provides the broader spectrum of radiation blocking;
- B. about 1.5 to 10.5% by weight of a plurality of dermatologically acceptable iron and zinc oxides having a particle size from about 0.3 to 10 microns. Preferably, the metal oxides include different kinds of iron oxides and zinc oxides;
- C. about 0.5 to 2.5% by weight of micronized talcum having a particle size of about 0.3 to 10 microns;
- D. about 4.5 to 10% by weight of antioxidants;
- E. about 1.5 to 5% by weight of a water soluble ultraviolet radiation block polymer;
- F. a selenium yeast complex; and
- G. at least one aqueous topical vehicle selected from the group consisting of ointments, suspensions, creams, lotions and emulsions.

The composition is formulated so as to provide an average SPF of at least about 70. By providing a range of particle sizes from 0.3 to 10 microns of the titanium oxide, iron oxides, zinc oxide and talc, a wide range of sunblocking is achieved without creating a noticeable mask. There is achieved a full spectrum of protection throughout the entire UVB–UVA range plus visible and infrared, namely, UVB= 290 nm–32 nm; UVA=320 nm–380 nm; visible=380/400 nm–650/700 nm; infrared—above 650/700 nm.

Preferably, different types of iron oxides are utilized, namely, red, yellow, black, brown and black-brown iron oxides. The compositions of the invention can be optimized when eight forms of milled solids in the micronized and ultramicronized ranges are utilized.

Sunblocking protection is further enhanced through the use of water soluble sunblocking polymers such as aluminum starch octenylsuccinate acrylate/octyacrylamide copolymer (DERMACRYL LT) which also helps in dispersion of the oxides.

The addition of up to about 3% by weight of UV protection boosters such as octyldodecyl neopentanate (tradename ELEFAC-I205k) enhances the UV protection factor and strengthens the atmospheric skin—shield effectiveness.

The addition of up to about 5% by weight of non-PABA radiation absorbers such as octyl methoxycinnamate (UVB), benzophenone-3 (UVB-mid UVA) and octocrylene (UVB-mid UVA) are used to assure continuous uninterrupted coverage.

Addition of at least 0.2 mg/g, preferably 1–5 mg/g, of a selenium protein complex such as selenium yeast complexes, sold under the trademark BIOMIN SE/P/C, by Brooks Industries, Inc., South Plainfield, N.J., have been demonstrated to increase minimal erythema dose-response while reducing acute skin cell damage due to UV exposure.

BIOMIN SE/P/C has a selenium content of about 0.1% and a polypeptide content of about 70%. The Biomins have been found to increase SPF about 16 to 25%.

The antioxidants which may be used in the compositions of the invention include tocopherol and tocopheryl acetate, ascorbyl acetate (Vitamin C derived) and beta carotene which are effective topical cellular protectants. The single most potent antioxidant is pycnogenol, a bioflavonoid like structure described in U.S. Pat. No. 4,698,360, which is herein incorporated by reference.

The composition according to this invention preferably includes the desired sunblocking ingredients in combination with one or more suitable topical ointments, creams, lotions or similar topical vehicles allowing for relatively even and dilute application of the active ingredient or ingredients to exposed surfaces of skin. A variety of commercially available topical vehicles are appropriate for use in this invention. Topical vehicles suitable for use in this invention can be selected from water, water-in-oil and oil-in-water emulsions of mineral, vegetable, animal and synthetic oils; petrolatum; glycerol; mineral; vegetable, animal and synthetic oils; propylene glycol; other aliphatic and aromatic alcohols which can be tolerated by the skin and many other vehicles suitable for topical application to skin.

The compositions according to this invention can also be enhanced by including other suitable additives in the topical mixtures. One preferred class of skin treatment compositions according to this invention uses a suitable in combination with a suitable chemical sunscreen, in particular sunscreens which are effective at reducing the intensity of ultraviolet radiation which reaches the skin. Sunscreens which may be suitable for use in the novel skin treatment compositions include in particular nonparamino benzoic acid sunscreens. Sunscreens are preferably included in the novel compositions in amounts sufficient to provide concentrations ranging from none to approximately 100 milligrams of sunscreen per millimeter of the topical mixtures. Concentration of the ultraviolet screening agent in amounts sufficient to provide sunscreen factors ranging from approximately 1 to approximately 30 are also indicative of the concentration of the ultraviolet screening agent which may be included. Examples of additional sunscreens which may be useful include octyl dimethyl PBA, octyl salicylate, palmitate, oxybenzone, and others. The suitable ultraviolet screening agent or agents are advantageously included to provide a sunscreen effect which is particularly effective and easy to apply in a routine manner prior to or during exposure to sunlight.

A variety of other additives may also be included in skin treatment compositions according to this invention for a variety of purposes. Ingredients for enhancing or providing humectant properties, spreadability, non-greasiness, fragrance, absorbability and many other desirable attributes of the novel skin treatment compositions can also be included.

The novel compositions can also be made by selecting, buying or manufacturing a suitable cream, lotion, suspension, ointment or other topical vehicle and then mixing the desired active ingredient or combination of active ingredients into the vehicle in the desired proportions. The active ingredients include the desired micronized particles, anti-oxidants and any suitable ultraviolet screening agent. Any desired additional such as described above are also mixed into the topical mixture in the desired concentrations.

The invention also includes novel methods for treating skin to reduce the risk of skin damage induced by sunlight or other source of ultraviolet radiation. The methods are useful in treatment mammals, more particularly primates, especially humans, both male and female. The novel methods include obtaining or preparing a suitable cream or other composition, such as described hereinabove. The compositions are applied to the skin in amounts sufficient to create effective application rates. The novel compositions are most preferably applied to healthy skin not opened by wound, disease or other affliction. The novel compositions are spread evenly onto the skin by the user's hands or with the aid of a suitable applicator, such as a brush, wand or other implement.

EXAMPLE I

A 1000 mg. batch of a composition of the invention was prepared by admixing the following ingredients in the following order:

| Ingredient | Wt. mg. |
| --- | --- |
| ELFAC I-205 | 25.0 |
| Polysorbate 20 | 30.0 |
| Tocopheryl Acetate | 5.0 |
| Sorbitan Laureate | 9.0 |
| COVI-OX T50 | 2.5 |
| Ascorby Palmitate | 0.5 |
| EMULGADE PL-1618 (CTFA) | 45.0 |
| DERMACRYL LT | 15.0 |
| UVINUL N-539 SG | 70.0 |
| PARSOL MCX | 60.0 |
| LIQUIPAR | 5.0 |
| Carotene in oil (30%) | 0.5 |
| TIOSPERSE TN | 75.0 |
| Z-Cote $HP_1$ | 32.6 |
| Water | QS |
| CAROMEL | 10.0 |
| Polysorbate 20 | 1.5 |
| FOAMINE 0-80 | 3.0 |
| Benzophenone-3 | 40.0 |
| Disodium EDTA | 1.0 |
| Antifoam FG-10 | 1.0 |
| Titanium Dioxide | 175.0 |
| Talc (Sugarload USP) | 60.0 |
| Cosmetic Red Iron Oxide | 2.7 |
| Cosmetic Yellow Iron Oxide | 2.3 |
| Cosmetic Brown Iron Oxide | 3.8 |
| Nonocat Superfine Iron Oxide | 0.4 |
| Propylene Glycol | 40.0 |
| Bonidox L | 3.0 |
| Dry Flo PC | 15.0 |

-continued

| Ingredient | Wt. mg. |
|---|---|
| Pycnogenol | 1.0 |
| Biomin SE/P/C | 1.0 |
| | 1000 mg |

The composition when applied provides an average SPF of at least 70.

COMPARATIVE EXAMPLE I

A study of 21 patients was conducted to determine the sweat resistance of the composition of Example I. The study was conducted pursuant to the standard test for sunscreen products according to the proposed monograph rules the FDA as reported in the Federal Register Vol. 43, No. 163 of Aug. 25, 1978, which is herein incorporated by reference.

The results are shown in the following Table:

TABLE 1

| | | Individual SPF Values | | |
|---|---|---|---|---|
| CPTC | Skin Type | 8% Homoslate Standard | Pre-sweating | Post-sweating |
| 8990 | III | 6.3 | 75.0 | 60.0 |
| 13178 | II | 5.0 | 75.0 | 60.0 |
| 728 | III | 5.0 | 60.0 | 60.0 |
| 1272 | II | 5.0 | 75.0 | 75.0 |
| 7624 | II | 5.0 | 75.0 | 75.0 |
| 12800 | II | 5.0 | 75.0 | 75.0 |
| 8907 | II | 4.0 | 75.0 | 75.0 |
| 1720 | II | 4.9 | 75.0 | 75.0 |
| 5678 | II | 4.9 | 75.0 | 75.0 |
| 10583 | II | 5.0 | 75.0 | 75.0 |
| 7285 | II | 4.9 | 75.0 | 75.0 |
| 13926 | II | 5.0 | 75.0 | 60.0 |
| 3760 | II | 5.0 | 60.0 | 60.0 |
| 12448 | II | 5.0 | 75.0 | 75.0 |
| 3414 | II | 5.0 | 60.0 | 60.0 |
| 3026 | III | 4.9 | 75.0 | 75.0 |
| 3656 | II | 4.9 | 75.0 | 75.0 |
| 2532 | II | 5.0 | 60.0 | 60.0 |
| 12278 | III | 5.0 | 75.0 | 75.0 |
| 12305 | II | ** | ** | ** |
| AverageSPF | | 49.9 | 72.75 | 70.50 |

CPTC# = Consumer Product Panelist Number
**Technical deviation from the protocol

EXAMPLE II

To a commercially available suntan lotion sold under the brand name COPPERTONE CREAM which has the following listed ingredients: palmitate and oxybenzyone as sunscreen agents, sorbitansesquioleate, sorbitol, glycerol stearate SE, isopropylmyristate, triethanolamine, octadecene/maleic anhydride copolymer, benzyl alcohol, lanolin, jajoba oil, cocoa butter, aloe extract, methyl paraben, propyl paraben, vitamin E acetate fragrance and water is added to the following:

| Ingredient | Wt % |
|---|---|
| Micronized Titanium Dioxides (6 types) | 5.0 |
| Micronized Iron Oxides (2 types) | 2.0 |
| Talc | 1.0 |

-continued

| Ingredient | Wt % |
|---|---|
| PYCNOGENOL (pure extract) | 3.0 |
| DERMACRYL LT | 1.5 |
| BIOMIN SE/P/C | 1.0 |

EXAMPLE III

A sweat resistant composition for protection against ultraviolet and infrared radiation can be prepared by admixing the following:
 A. about 1.5 to 10.5% by weight of micronized and ultramicronized titanium dioxide particles having particle sizes from about 0.3 to 10 microns;
 B. about 0.5 to 2.5% by weight of a plurality of iron oxides having a particle size of about 0.3 to 10 microns;
 C. about 0.5 to 2.5% by weight of talcum having a particle size of about 0.3 to 10 microns;
 D. about 4.5 to 10% by weight of antioxidants selected from the group consisting of tocopherol, tocopherol acetate, ascorbic acetate and beta carotene;
 E. about 0.5 to 1.5% by weight of aluminum starch octenylsuccinate acrylate/octyacrylamide copolymer;
 F. about 1.0 mg. of BIOMIN SE/P/C; and
 G. an aqueous topical lotion.

The topical lotion can be a commercially available sunscreen lotion such as sold under the brand names SEA and SKI, HAWAIIAN TROPIC and the like.

What is claimed is:

1. In a sunblocking composition containing sunscreening materials the improvement which comprises an effective amount of a selenium yeast complex to increase the SPF value of the composition.

2. The sunblocking composition of claim 1 which comprises:
 A. about 1.5 to 10.5% by weight of micronized and ultramicronized titanium dioxide particles having a variety of particle sizes from about 0.3 to 10 microns;
 B. about 0.5 to 2.5% by weight of a plurality of iron oxides and zinc oxides having a particle size of about 0.3 to 10 microns;
 C. about 0.5 to 2.5% by weight of talcum having a particle size of about 0.3 to 10 microns;
 D. about 4.5 to 10% by weight of antioxidants selected from the group consisting of tocopherol, tocopherol acetate, ascorbic acetate and beta carotene;
 E. about 0.5 to 1.5% by weight of aluminum starch octenylsuccinate acrylate/octyacrylamide copolymer;
 F. an aqueous topical lotion
 G. a UV absorber selected from the group consisting of octyl methoxycinnamate, benzophenone-3 and octocrylene; and
 H. wherein the selenium yeast complex is present in an amount of about 1 to 5 mg/g, said composition having at least eight forms of milled solids, said composition having a SPF of at least about 70.

3. The composition of claim 2 wherein said iron oxide is selected from the group consisting of red iron oxide, brown iron oxide and black iron oxide.

4. The composition of claim 2 comprising nanometer ultramicronized brown iron oxide and micronized red, yellow and brown-black iron oxide.

* * * * *